United States Patent
McKay

(10) Patent No.: US 8,162,992 B2
(45) Date of Patent: Apr. 24, 2012

(54) SPINAL FUSION WITH OSTEOGENIC MATERIAL AND MIGRATION BARRIER

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1192 days.

(21) Appl. No.: 11/120,152

(22) Filed: Apr. 30, 2005

(65) Prior Publication Data

US 2006/0247783 A1 Nov. 2, 2006

(51) Int. Cl.
*A61B 17/88* (2006.01)
*A61F 2/44* (2006.01)

(52) U.S. Cl. .............. 606/279; 623/17.11; 623/17.16

(58) Field of Classification Search .......... 623/17.11, 623/17.16; 606/279
See application file for complete search history.

(56) References Cited

U.S. PATENT DOCUMENTS

| | | | | |
|---|---|---|---|---|
| 5,782,830 A | * | 7/1998 | Farris | 606/99 |
| 6,033,438 A | * | 3/2000 | Bianchi et al. | 623/17.16 |
| 6,126,688 A | * | 10/2000 | McDonnell | 623/17.16 |
| 6,508,839 B1 | * | 1/2003 | Lambrecht et al. | 623/17.16 |
| 2001/0008980 A1 | | 7/2001 | Gresser et al. | |
| 2001/0016646 A1 | * | 8/2001 | Rueger et al. | 530/840 |
| 2002/0026244 A1 | * | 2/2002 | Trieu | 623/17.16 |
| 2002/0173851 A1 | * | 11/2002 | McKay | 623/17.11 |
| 2003/0074075 A1 | * | 4/2003 | Thomas et al. | 623/17.16 |
| 2004/0225360 A1 | | 11/2004 | Malone | |
| 2004/0230309 A1 | * | 11/2004 | DiMauro et al. | 623/17.12 |
| 2005/0070900 A1 | * | 3/2005 | Serhan et al. | 606/61 |

\* cited by examiner

*Primary Examiner* — Eduardo C Robert
*Assistant Examiner* — Julianna N Harvey

(57) ABSTRACT

Described are interbody spinal fusion methods, and kits useful therefor, in which a barrier material is interposed between an osteogenic material and an opening in the disc annulus providing access to the interbody space, wherein the barrier material is effective to inhibit migration of the osteogenic substance to the opening.

22 Claims, 1 Drawing Sheet

SPINAL FUSION WITH OSTEOGENIC MATERIAL AND MIGRATION BARRIER

BACKGROUND

The present invention relates generally to spinal fusion methods. In particular aspects, the invention relates to spinal fusion methods employing an osteogenic material delivered to the interbody space along with a barrier material positioned to inhibit migration of the osteogenic material.

As further background, intervertebral discs, located between the endplates of adjacent vertebrae, stabilize the spine, distribute forces between vertebrae, and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease or aging. Disruption of the annulus fibrosus allows the nucleus pulposus to protrude into the vertebral canal, a condition commonly referred to as a herniated or ruptured disc. The extruded nucleus pulposus may press on a spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

In certain instances, the only relief from the symptoms of these conditions is a discectomy, or surgical removal of a portion or all of an intervertebral disc, followed by fusion (arthrodesis) of the adjacent vertebrae. For these purposes, loadbearing implants are often used to maintain the disc space while new bone growth and arthrodesis are achieved. A variety of such implants have been suggested and/or used, including hollow spinal cages that can be filled with osteogenic material, prior to insertion into the intervertebral space. Apertures defined in the cage communicate with the hollow interior to provide a path for tissue growth between the vertebral endplates. Interbody spinal implants fabricated from bone have also been employed. These include for instance threaded bone dowel products and impacted spacers. An osteogenic substance is typically implanted in conjunction with these spacers to achieve fusion.

Minimally-invasive spinal fusion procedures have been developed, including those involving anterior surgical approaches, e.g. using laproscopic instrumentation, and those involving posterior surgical approaches, e.g. using introducer sleeves. In these approaches, surgical access is provided to the interbody space through the cannulated device (e.g. laproscope or sleeve), and one or more loadbearing implants are introduced through the cannulated device. Oftentimes, the surgeon will pack an osteogenic graft material into an opening or recess in the loadbearing implant prior to introduction and/or in and around the implant, to assist in the fusion process. Access to the surgical field in the interbody space can be somewhat limited, especially in minimally invasive procedures. Nonetheless, techniques for implant and graft placement and retention need to be conducted in a manner that ensures the opportunity for a positive surgical outcome.

In light of this background, there exist needs for improved and/or alternative devices, techniques and systems that are useful for the conduct of interbody spinal fusion procedures. The present invention addresses these needs.

SUMMARY

In one aspect, the present invention provides an interbody spinal fusion method that included providing surgical access to an interbody space between first and second adjacent vertebral bodies, the access including at least one opening in a wall of a disc annulus defining the interbody space. A loadbearing spinal spacer is introduced into the interbody space through the opening, and an osteogenic substance is delivered to the interbody space through the opening. A barrier material is also delivered, e.g. through, into and/or around the opening, so as to inhibit the migration of the osteogenic substance out of the opening. In certain embodiments of the invention, the barrier material is delivered to the interbody space through the opening at least to a position between the osteogenic substance and the opening. The barrier material is delivered sufficiently to inhibit migration of the osteogenic substance to the opening. In certain inventive aspects, the fusion method is a minimally-invasive method involving the placement of a cannulated device, such as an anterior or posterior guide tube, through soft patient tissues to provide surgical access to the interbody space. As well, the osteogenic substance is desirably a material including a recombinant human bone morphogenic protein and a carrier matrix, and the barrier material desirably comprises a resorbable biological or synthetic polymer. In certain forms of the invention, the osteogenic material and the barrier material are separately delivered through tubular delivery devices, such as syringes.

In another embodiment, the present invention provides a medical kit that is useful for the performance of an interbody spinal fusion procedure. The medical kit includes a loadbearing interbody spinal spacer, an osteogenic protein, a carrier material combinable with the osteogenic protein to form an osteogenic implant material, and a barrier material effective to inhibit migration of the osteogenic implant material. The kit can include one or more additional components including for example at least one syringe device for delivery of the osteogenic substance and at least one syringe for delivery of the barrier material. These and other items of the kit can be sealed in medical packaging together in a sterile condition.

Additional embodiments as well as features and advantages of the invention will be apparent to those of ordinary skill in the art from the further descriptions herein.

BRIEF DESCRIPTION OF THE FIGURES

Various embodiments of the present invention will be discussed with reference to the appended drawings. These drawings depict only illustrative embodiments of the invention and are not to be considered limiting of its scope.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations and further modifications in the described embodiments, and such further applications of the principles of the invention as illustrated therein being contemplated as would normally occur to one skilled in the art to which the invention relates.

As disclosed above, the present invention provides methods, assemblies and kits that are useful for the conduct of interbody spinal fusion procedures. In particular aspects of the invention, interbody spinal fusion procedures are provided that involve the use of a barrier material to inhibit undesired migration of an osteogenic substance used in the procedure.

Figure 1:
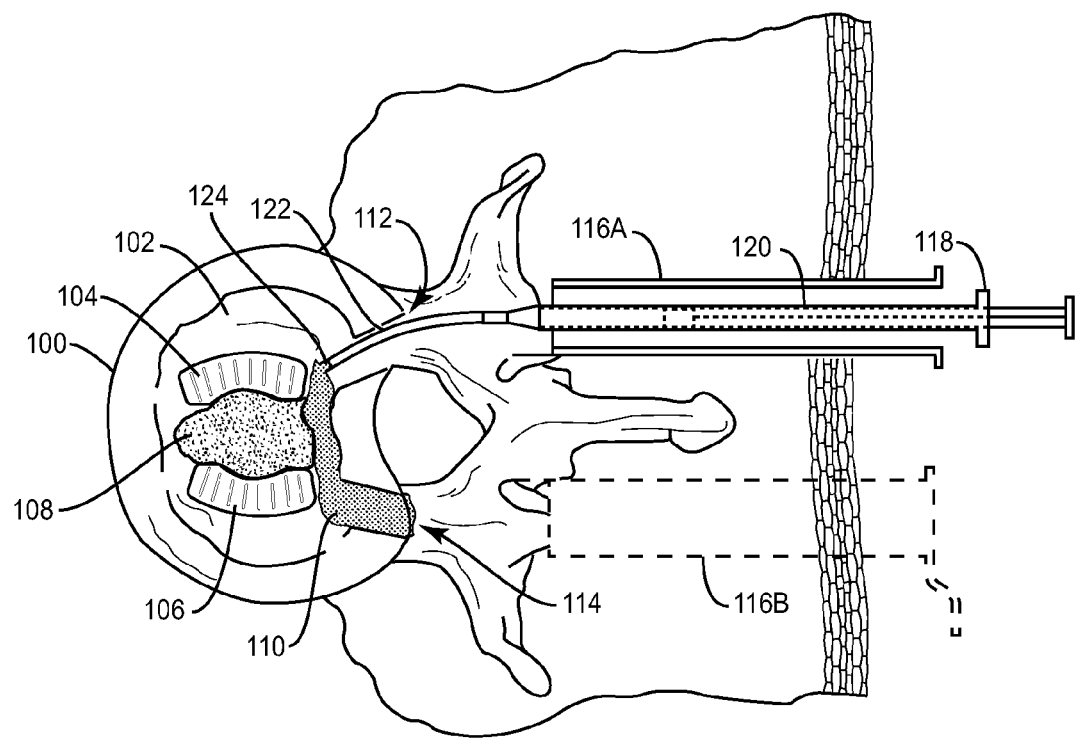
FIG. 1 depicts a stage in the conduct of an interbody spinal fusion procedure of the present invention using a minimally-invasive posterior access.

Referring now FIG. 1, depicted is a stage of an illustrative spinal fusion procedure of the present invention. The depicted procedure represents a type of posterior-access minimally-invasive procedure, in which access to the interbody space 102 within spinal disc 100 is provided using a posterior approach. A first spinal spacer 104 and a second spinal spacer 106 are positioned within the interbody space 102 and maintain a disc height for the fusion. Spacers 104 and 106 can, for example, be threaded or impacted spacers made of metal, bone, or any other suitable material. In one embodiment, spacers 104 and 106 are impacted bone wedges spacers such as those commercially available as the Tangent™ spacer (Medtronic Sofamor Danek, Memphis, Tenn. USA). An amount of osteogenic material 108 has been delivered into the interbody space 102 in and around spacers 104 and 106, to facilitate the development of a fusion mass of bone. An amount of a barrier material 110 (non-osteogenic, and desirably a substantially inert substance) has been delivered to a location posterior of the osteogenic substance 108, forming a barrier that inhibits the posterior migration of the osteogenic substance 108 to opening 112 providing access to the interbody space 102. As to the location and extent of barrier material 110, desirably, material 110 will be delivered so as to extend at least substantially across the dimension of the opening 112 (and 114) and desirably completely across and even exceeding the dimension of the opening 112 (and 114). In certain embodiments, the barrier material can be delivered sufficiently to extend substantially across the dimension of the posterior wall of the disc 100, for instance encompassing at least about 50% of such dimension and potentially higher levels including for instance about 60-100% of such dimension in some cases. As well, amounts of barrier material 110 can be placed at still other locations within the interbody space 102 to facilitate retention of the original position of the osteogenic substance 108 and thereby regulate the position and extent of the formed bone fusion column or mass.

In the illustrated procedure, access to the interbody space has been achieved through a minimally-invasive posterior approach including the placement of first and second introducer sleeves or guide tubes 116A and 116B. The access and instrumentation used for the procedure may be facilitated, for example using Minimal Spinal Access Technology (MAST) products available from Medtronic Sofamor Danek, Inc. (Memphis, Tenn.), including for instance the METRx™ X-Tube™ retraction system. Thus, cannulated elements 116A and 116B may be X-Tube™ guide tubes. Such tubes can be positioned within soft patient tissues after incision and passage of a series of tissue dilators of increasing size (available as a part of the above-mentioned MAST products and technology) to create an opening for the cannulated device. Oftentimes, a laminectomy is performed, in which at least a portion of the lamina will be excised from a vertebra occurring above the disc space to be accessed. Potentially also, the procedure can involve excision of at least a portion of an articular facet (facetectomy) or other bony structures as necessary for surgical access. After access to the disc space is gained, patient disc tissue can be excised, and the vertebral endplates can be decorticated using minimally invasive instrumentation prior to introduction of the spacers and osteogenic material. As depicted in FIG. 1, such procedures as well as the introduction of barrier material have already occurred through sleeve 116B, and similar procedures are under way through sleeve 116A.

At the stage shown in FIG. 1, a needleless syringe device 118 has been passed through sleeve 116A to position its distal tip within the posterior portion of the interbody space 102. Syringe device 118 has a body including a generally straight portion 120 and a distally-attached flexible tube having or capable of forming a bend 122 to facilitate placement of a barrier material 110 transportable therethrough in the desired regions. It will be understood in this regard that a similar and preferably separate syringe device 118 can be used to deliver some or all of the osteogenic material 108 into the interbody space 102. As well, it will be understood that other syringe configurations, including straight syringes, can be used to deliver the osteogenic material 108 and/or the barrier material 110, and that in certain embodiments such syringe(s) can include one or more imagable (e.g. radiopaque) markers, such as marker band 124, adjacent to their distal tips so that their positioning can be monitored with an external imaging system such as an X-ray, magnetic resonance imaging (MRI), or ultrasonic imaging system. Further, in alternative embodiments, one or both of the osteogenic material 108 and the barrier material 110 can be delivered through sleeves 116A and 116B and placed using forceps or any other suitable surgical manipulation device. This may occur, for instance, where such material(s) are of a more solid (e.g. sheet or body) structure and would not be readily transportable through a syringe-type device.

Figure 2:
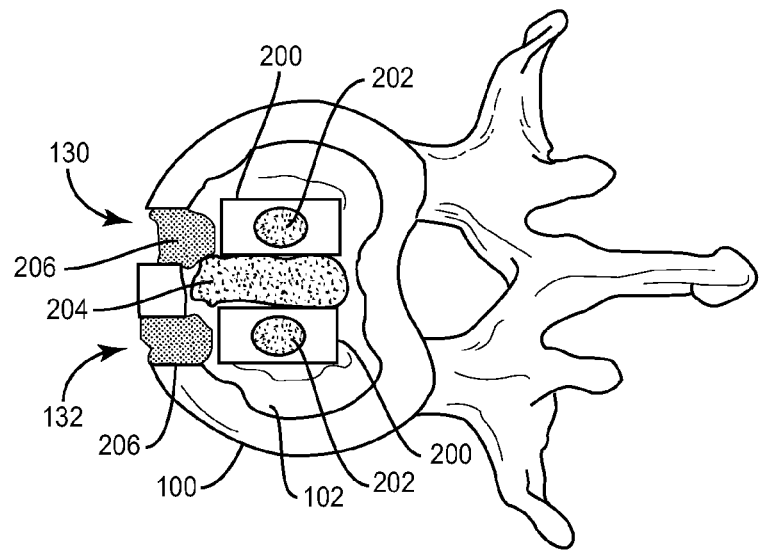
FIG. 2 depicts a stage in the conduct of an interbody spinal fusion procedure of the present invention using a minimally-invasive anterior access.

With reference now to FIG. 2, shown is a stage of a spinal fusion procedure of the invention conducted through an anterior approach to disc 100 and interbody space 102, through openings 130 and 132 (or a single, larger opening) in the disc annulus defining the interbody space. Implanted spacers 200 can, for example, be a threaded or impacted cage or other spinal spacer made of metal, bone or any other suitable material. Illustratively, spacers 200 can be tapered metal cage devices such as the LT Cage® lumbar tapered fusion device or bone dowels such as MD-I, MD-II and/or MD-III cortical allograft dowels, available from Medtronic Sofamor Danek. The surgical approach can be a minimally invasive approach as well, using an anterior lumbar interbody fusion guide tube and other instrumentation also available from Medtronic Sofamor Danek. The surgical procedure involves the delivery of an amount of osteogenic material, which can include osteogenic material 202 (e.g. Infuse™ Bone Graft material including rhBMP-2 and absorbable collagen sponge) within the spacer 200 and optionally also osteogenic material 204 external of the spacer 200. In accordance with aspects of the present invention, barrier material 206 can be delivered so as to extend at least substantially across the dimension of the opening(s) in the anterior disc wall (e.g. 130 and 132) and desirably completely across and even exceeding the dimension of the opening(s). In certain embodiments, the barrier material can be delivered sufficiently to extend substantially across the dimension of the anterior wall of the disc 100, for instance encompassing at least about 50% of such dimension and potentially higher levels including for instance about 60-100% of such dimension in some cases. As well, as discussed above, amounts of barrier material 206 can be placed at still other locations within the interbody space 102 to facilitate retention of the original position of the osteogenic substance 108 and thereby regulate the position and extent of the formed bone fusion mass.

It will be understood other types of minimally-invasive access surgeries through small incisions (e.g. about 30 mm or less) can also be used in the invention, including for instance minimally invasive laproscopic anterior surgical approaches, minimally invasive transforaminal surgical approaches, minimally invasive lateral fusion approaches, and mini-open surgical approaches. In certain embodiments, open surgeries can also be performed. In such minimally invasive or other surgeries, the opening or openings in the annulus fibrosus can occur in an anterior, posterior, and/or lateral walls thereof.

Any suitable osteogenic material can be used in methods of the invention, including for instance harvested autologous bone or other suitable osteogenic substances. In certain embodiments, the osteogenic substance can include a growth factor that is effective in inducing formation of bone. Desirably, the growth factor will be from a class of proteins known generally as bone morphogenic proteins (BMPs), and can in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in U.S. Pat. Nos. 5,965,403 and 6,331,612. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these patents and applications are hereby incorporated herein by reference. Also useful in the present invention are heterodimers of the above and modified proteins or partial deletion products thereof. These proteins can be used individually or in mixtures of two or more. rhBMP-2 is preferred.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size and nature of the defect being treated, and the carrier and particular protein being employed. In certain embodiments, the amount of osteogenic protein to be delivered will be in a range of from about 0.05 to about 1.5 mg.

Other therapeutic growth factors may also be used in accordance with the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-α and TGF-β.

The osteogenic proteins or other biologically active agents to be used in the present invention can be delivered as liquid formulations, for example buffered aqueous formulations. In certain embodiments, such formulations are mixed with, received upon and/or within, or otherwise combined with a carrier material.

In this regard, the carrier is collagenous in certain embodiments, desirably taking the form of a resorbable porous matrix. A wide variety of collagen materials are suitable for form such a resorbable matrix. Naturally occurring collagens may be subclassified into several different types depending on their amino acid sequence, carbohydrate content and presence or absence of disulfide cross-links. Types I and III collagen are two of the most common subtypes of collagen. Type I collagen is present in skin, tendon and bone whereas Type III collagen is found primarily in skin. The collagen in the matrix may be obtained from skin, bone, tendon, or cartilage and purified by methods known in the art. Alternatively, the collagen may be purchased commercially. The porous matrix composition desirably includes Type I bovine collagen.

The collagen of a carrier matrix can further be atelopeptide collagen and/or telopeptide collagen. Moreover, non-fibrillar and/or fibrillar collagen may be used. Non-fibrillar collagen is collagen that has been solubilized and has not been reconstituted into its native fibrillar form.

Suitable carrier materials may also be formed of other organic materials such as natural or synthetic polymeric materials, in addition to or as an alternative to collagen. For example, the resorbable carrier may comprise gelatin (e.g. foamed gelatin), demineralized bone matrix (DBM), or resorbable synthetic polymers such as polylactic acid polymers, polyglycolic acid polymers, or co-polymers thereof. Other natural and synthetic polymers are also known for the formation of biocompatible resorbable matrix materials, and can be used in the invention.

The carrier may also be or include a natural and/or synthetic mineral component. For example, the mineral component can be provided by a particulate mineral material, including either powder form or larger particulate mineral materials. In certain embodiments, the particulate mineral component is effective in providing a scaffold for bone ingrowth as the resorbable matrix material is resorbed. The mineral material may for example be bone, especially cortical bone, or a synthetic bioceramic such as a biocompatible calcium phosphate ceramic. Illustrative ceramics include tricalcium phosphate, hydroxyapatite, and biphasic calcium phosphate. These mineral components may be purchased commercially or obtained or synthesized by methods known in the art.

As noted above, biphasic calcium phosphate can be used to provide a mineral-containing carrier in the invention. Desirably, such biphasic calcium phosphate will have a tricalcium phosphate:hydroxyapatite weight ratio of about 50:50 to about 95:5, more preferably about 70:30 to about 95:5, even more preferably about 80:20 to about 90:10, and most preferably about 85:15.

The carrier can include an amount of mineral that will provide a scaffold effective to remain in a patient for a period of time sufficient for the formation of osteoid in the void for which bone growth is desired. The minimum level of mineral that must be present in the carrier for these purposes is also dependent on the level of activity of the tissue growth promoting components in the isolate and whether other substances such as BMP or other osteogenic proteins are incorporated into the carrier in combination with the tissue growth promoting components of the isolate.

In certain forms of the invention, the carrier may include a particulate mineral component embedded in a porous organic matrix formed with a material such as collagen, gelatin or a resorbable synthetic polymer. In this regard, the particulate mineral:resorbable porous matrix weight ratio of the first implant material may be at least about 4:1, more typically at least about 10:1. In highly mineralized carriers, the particulate mineral will constitute at least 95% by weight of the first implant material. For example, carrier materials may be provided comprising about 97% to about 99% by weight particulate mineral and about 1% to about 3% of the collagen or other matrix forming material. Moreover, the mineral component may for example have an average particle size of at least about 50 microns, more preferably about 0.5 mm to about 5 mm, and most preferably about 1 mm to about 3 mm.

Carriers used may be non-dimensionally-stable, for example as in flowable or malleable substances such as liquids or pastes. Illustratively, the carrier may include a biologically resorbable, non-dimensionally-stable material having properties allowing its implantation and retention at a tissue defect site. Such carriers can include resorbable organic materials such as macromolecules from biological or synthetic sources, for example gelatin, hyaluronic acid carboxymethyl cellulose, collagen, peptides, glycosaminoglycans, proteoglycans, and the like. Such materials can be used with or without an incorporated particulate mineral component as described hereinabove. In certain forms, the resorbable carrier can be formulated into the composition such that the composition is flowable at temperatures above the body temperature of a patient into which the material is to be implanted, but transitions to be relatively non-flowable at or slightly above such body temperature. The resorbable carrier may be formulated into the implanted composition so the flowable state is a liquid or a flowable gel, and the non-flowable state is a stable gel or solid. In certain embodiments of the invention, the resorbable carrier can include gelatin, and/or can incorporate a particulate mineral in an amount that constitutes about 20% to about 80% by volume of the carrier composition, more typically about 40% to about 80% by volume.

As noted above, implant materials used in the invention can incorporate an osteogenic protein carried by the implant carrier material, for example received upon and/or within the carrier material, either in a dry form that can be delivered or in a liquid formulation retained by the carrier or mixed with the carrier.

In certain specific embodiments, the osteogenic protein formulation or other medical formulation will be provided as a liquid formulation which is received within the pores of a compressible carrier material. The compressible carrier material can be a generally three-dimensionally-stable body material such as a spongiform material which may or may not exhibit shape memory after compression, e.g., in the latter case exhibiting properties consistent with a stiff porous putty which is subject to deformation, especially when wet, that compresses the pores of the material. In other embodiments, the carrier can be a non-three-dimensionally-stable carrier material such as a paste. In any of these embodiments, the application of force to the carrier material can compress the material and cause liquid formulation received therein to separate from the carrier material, for example by expressing the liquid formulation from the internal spaces which are compressed. Where this is the case, it can be desirable to deliver the material in a fashion in which separation of the liquid and the carrier matrix is avoided. For example, needleless syringe devices with constant or increasing (in the direction of the distal opening) internal barrel diameters can be used with advantage when delivering such implant materials to patients, as they facilitate the advancement of the compressible carrier material through the delivery lumen of the syringe barrel with minimal or no compression whereby expression of the liquid formulation from pores of the compressible material is minimized or prevented.

In embodiments wherein a liquid formulation is received within a compressible carrier material, the liquid formulation can be combined with the carrier material in any suitable manner and at any suitable point during manufacture or in the surgical field. For example, in certain embodiments a surgeon or other health care provider can apply a liquid formulation of a medical agent onto and into the carrier material prior to implant by soaking, spraying or otherwise. In other embodiments, the carrier material in dry form may include dried amounts of the medical agent, and can thereafter be wetted whereupon liquid within pores of the carrier material will contain dissolved or suspended amounts of the medical agent. In either case, this liquid formulation-containing compressible carrier material can be loaded into a syringe device and delivered to desired implant locations such as the interbody space between adjacent vertebra. Alternately, such osteogenic materials can be delivered with forceps or another surgical instrument.

Other biologically active materials may also be used in conjunction with methods of the present invention. These include for example cells such as human allogenic or autologous chondrocytes, human allogenic cells, human allogenic or autologous bone marrow cells, human allogenic or autologous stem cells, demineralized bone matrix, insulin, insulin-like growth factor-1, interleukin-1 receptor antagonist, hepatocyte growth factor, platelet-derived growth factor, and Indian hedgehog and parathyroid hormone-related peptide, to name a few.

The barrier material utilized in the present invention can be any suitable material effective to prevent or at least substantially inhibit the migration of the osteogenic material. Illustratively, in certain aspects, the barrier material can be provided by materials described hereinabove as carriers, except not including any osteogenic factor and desirably remaining relatively inert in the implant environment. In certain embodiments the barrier material will comprise a biodegradable synthetic polymer, in either flowable (and potentially hardenable) or non-flowable form. Illustratively, preferred barrier materials can have a first relatively flowable state during delivery and a second relatively less flowable state after implantation. For example, the barrier material may remain in an uncured, deformable, or otherwise configurable state during introduction to the intervertebral disc space, and rapidly cure, become harder or solidify after being introduced. Suitable materials that may be used for the barrier material include tissue sealants, adhesives, or implant materials made from natural or synthetic materials, including, for example, fibrin, albumin, collagen, elastin, silk and other proteins, polyethylene glycols (e.g. PEG gels), polyethylene oxide, cyanoacrylate, polylactic acid, polyglycolic acid, copolymers of polylactic acid and polyglycolic acid, polypropylene fumarate, tyrosine-based polycarbonate, ceramics, and combinations thereof. The barrier material can be delivered to the desired, migration-inhibiting site or region in any suitable fashion, including in certain instances flow-based delivery modes such as advancement through and out of tubular devices such as syringe devices or spray devices. The migration-inhibiting site or region can be selected to include locations within the interbody space, and/or within an opening or openings in the annulus fibrosus defining the interbody space at which the fusion is undertaken, and/or over the outside of the annulus fibrosus and covering the opening or openings.

In some embodiments of the invention, these or other suitable materials can be used as sheets or other pre-formed bodies, porous or non-porous, but desirably conformable, which can be introduced into the interbody space to serve as barrier materials. Such a barrier body can optionally include an adhesive coating over all or a portion of its surface to aid in maintaining the body at a desired implanted location. Illustrative implantable barrier bodies include for instance cast or molded reconstituted collagen bodies, including reconstituted collagen sheets (porous or non-porous), formed fibrin clot bodies, natural tissue sheets (e.g. fat, pericardium, smal intestinal submucosa (SIS)), biodegradable polymer bodies, including cast layers and sponges, and others known to those skilled in the art. Such implantable bodies can be introduced and packed into and/or placed over appropriate regions sufficiently to prevent or inhibit the migration of the osteogenic material used in the fusion procedure and in particular its escape from an opening or openings in the annulus fibrosus.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents and patent applications cited in this specification are herein incorporated by reference as if each individual publication, patent or patent application was specifically and individually indicated to be incorporated by reference as set forth in its entirety herein.

What is claimed is:

1. An interbody spinal fusion method, comprising providing surgical access to an interbody space between first and second adjacent vertebral bodies, said access including at least one opening in a wall of a disc annulus defining the interbody space;
   introducing a first loadbearing spinal spacer and a second loadbearing spinal spacer into the interbody space through said at least one opening, wherein the first and second loadbearing spacers comprise bone or metal;
   delivering an osteogenic substance to said interbody space through said opening so as to promote bone growth to fuse said first and second adjacent vertebral bodies to one another, wherein said osteogenic substance is delivered in a carrier material containing osteogenic protein to a space in and around said first loadbearing spinal spacer and said second loadbearing spinal spacer; and
   delivering a flowable, biodegradable barrier material by flow through a tubular delivery device so as to inhibit migration of said osteogenic substance from said opening, wherein the barrier material (i) extends at least 50% along the dimension of either a posterior or anterior wall of the disc and (ii) contacts a portion of said osteogenic substance to inhibit migration but does not surround all of said osteogenic substance, wherein the biodegradable barrier material comprises a ceramic material, and wherein during delivery the barrier material has a first state and after delivery the barrier material has a second state, wherein said first state is more flowable than said second state.

2. The method of claim 1 wherein said access further includes a cannulated device positioned through soft tissues of the patient.

3. The method of claim 1 wherein the osteogenic protein comprises a bone morphogenic protein (BMP) or a growth differentiation factor (GDF).

4. The method of claim 3 wherein the BMP comprises a recombinant human BMP.

5. The method of claim 4 wherein the BMP comprises recombinant human BMP-2.

6. The method of claim 1 wherein the osteogenic substance comprises autograft bone.

7. The method of claim 1, wherein the osteogenic substance is delivered through a syringe device.

8. The method of claim 1, wherein the barrier material is delivered to a site within the interbody space, within the opening, and/or over the opening.

9. The method of claim 8, wherein said second state is a gel or non-flowable solid state.

10. The method of claim 1 wherein said barrier material comprises a natural or synthetic polymer.

11. A method for interbody spinal fusion in a patient, comprising:
    providing surgical access to an interbody space between first and second adjacent vertebral bodies, said access including at least one opening in a posterior wall of a disc annulus defining the interbody space;
    introducing a first loadbearing spinal spacer and a second loadbearing spinal spacer into the interbody space through said at least one opening, wherein the first and second loadbearing spacers comprise bone or metal;
    delivering an osteogenic substance in a carrier material containing an osteogenic protein to said interbody space through said opening so as to promote bone growth to fuse said first and second adjacent vertebral bodies to one another, wherein said osteogenic substance is delivered to a space in and around said first loadbearing spinal spacer and said second loadbearing spinal spacer; and
    delivering a flowable, biodegradable barrier material by flow through a tubular delivery device to a position posterior of said osteogenic substance, said barrier material delivered in an amount and at a location so as to inhibit posterior migration of said osteogenic substance from said opening, wherein the barrier material (i) extends at least 50% along the dimension of the posterior wall of the disc and (ii) contacts a portion of said osteogenic substance to inhibit migration but does not surround all of said osteogenic substance, wherein the biodegradable barrier material comprises a ceramic material, and wherein during delivery the barrier material has a first state and after delivery the barrier material has a second state, wherein said first state is more flowable than said second state.

12. The method of claim 11 wherein said access further includes a cannulated device positioned through soft tissues of the patient.

13. The method of claim wherein the osteogenic protein comprises a recombinant human BMP.

14. The method of claim 13 wherein the osteogenic protein comprises recombinant human BMP-2.

15. The method of claim 13, wherein both the osteogenic substance and the barrier material are delivered through a syringe device.

16. The method of claim 15 wherein said barrier material is resorbable and comprises a natural or synthetic polymer.

17. An interbody spinal fusion method, comprising:
providing surgical access to an interbody space between first and second adjacent vertebral bodies, said access including at least one opening in an anterior wall of a disc annulus defining the interbody space;
introducing a first loadbearing spinal spacer and a second loadbearing spinal spacer into the interbody space through said at least one opening, wherein the first and second loadbearing spacers comprise bone or metal;
delivering an osteogenic substance in a carrier material containing an osteogenic protein to said interbody space through said opening so as to promote bone growth to fuse said first and second adjacent vertebral bodies to one another, wherein said osteogenic substance is delivered to a space in and around said first loadbearing spinal spacer and said second loadbearing spinal spacer; and
delivering a flowable, biodegradable barrier material by flow through a tubular delivery device to a position anterior of said osteogenic substance, said barrier material delivered in an amount and at a location so as to inhibit anterior migration of said osteogenic substance from said opening, wherein the barrier material (i) extends at least 50% along the dimension of the anterior wall of the disc and (ii) contacts a portion of said osteogenic substance to inhibit migration but does not surround all of said osteogenic substance, wherein the biodegradable barrier material comprises a ceramic material, and wherein during delivery the barrier material has a first state and after delivery the barrier material has a second state, wherein said first state is more flowable than said second state.

18. The method of claim 17 wherein said access further includes a cannulated device positioned through soft tissues of the patient.

19. The method of claim 17 wherein the osteogenic protein comprises a recombinant human BMP.

20. The method of claim 19 wherein the osteogenic protein comprises recombinant human BMP-2.

21. The method of claim 19, wherein both the osteogenic substance and the barrier material are delivered through a syringe device.

22. The method of claim 21 wherein said barrier material is resorbable and comprises a natural or synthetic polymer.

\* \* \* \* \*

UNITED STATES PATENT AND TRADEMARK OFFICE
CERTIFICATE OF CORRECTION

PATENT NO.        : 8,162,992 B2
APPLICATION NO.   : 11/120152
DATED             : April 24, 2012
INVENTOR(S)       : McKay Page 1 of 1

It is certified that error appears in the above-identified patent and that said Letters Patent is hereby corrected as shown below:

In Column 10, Line 21, in Claim 8, delete "and/or" and insert -- and --, therefor.

In Column 10, Line 61, in Claim 13, delete "claim" and insert -- claim 11 --, therefor.

Signed and Sealed this
Fourth Day of September, 2012

David J. Kappos
*Director of the United States Patent and Trademark Office*